US008273035B2

(12) United States Patent (10) Patent No.: US 8,273,035 B2
Russo et al. (45) Date of Patent: Sep. 25, 2012

(54) HUMAN BIOVIBRATIONS METHOD

(75) Inventors: Michael B. Russo, Honolulu, HI (US); Alexander H. Vo, Houston, TX (US); Daniel P. Redmond, Silver Spring, MD (US); Robert Conlan, Fort Walton Beach, FL (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 608 days.

(21) Appl. No.: 12/242,540

(22) Filed: Sep. 30, 2008

(65) Prior Publication Data

US 2009/0149779 A1 Jun. 11, 2009

Related U.S. Application Data

(63) Continuation-in-part of application No. PCT/US2007/008219, filed on Apr. 2, 2007.

(60) Provisional application No. 60/788,759, filed on Apr. 1, 2006.

(51) Int. Cl.
*A61B 5/00* (2006.01)
*A61B 5/103* (2006.01)
*A61B 5/11* (2006.01)
*A61B 5/113* (2006.01)
*G08B 23/00* (2006.01)

(52) U.S. Cl. ........ 600/595; 600/300; 600/301; 600/324; 600/484; 600/587; 340/575; 702/19

(58) Field of Classification Search ................... 600/300, 600/587, 595, 301, 324, 484; 340/575; 702/19
See application file for complete search history.

(56) References Cited

U.S. PATENT DOCUMENTS 4,757,825 A 7/1988 Diamond
(Continued)

FOREIGN PATENT DOCUMENTS

WO WO 2007117402 10/2007

OTHER PUBLICATIONS

Russo, M. B. Human Biovibrations: Assessment of Human Life Signs, Motor Activity, and Cognitive Performance Using Wrist-Mounted Actigraphy. Aviation, Space and Environmental Medicine. Jul. 2005, vol. 76, No. 7, Section II, pp. C64-C74.

(Continued)

*Primary Examiner* — Sean Dougherty
(74) *Attorney, Agent, or Firm* — Marcus Streips

(57) ABSTRACT

This invention relates to the detection of human biovibrations using a digital signal processing (DSP) actigraph worn by the individual, and in at least one method using any noise existing in the signals. Human biovibrations result from the human body having reverberations and oscillations from bodily functioning. The DSP actigraph has been shown to be able to identify heart beat and breathing of an individual. The invention includes a method comprising: recording movement data of an individual that includes biovibrations data, determining when the movement data substantially falls within a predetermined threshold representative of death, and providing a notification. The invention in at least one embodiment includes a method comprising: monitoring activity counts for zero crossing mode, above threshold mode, and proportional integrative mode, providing a notification when all three activity counts are within a respective predetermined range for a period of time.

20 Claims, 8 Drawing Sheets

U.S. PATENT DOCUMENTS

Figure 1:
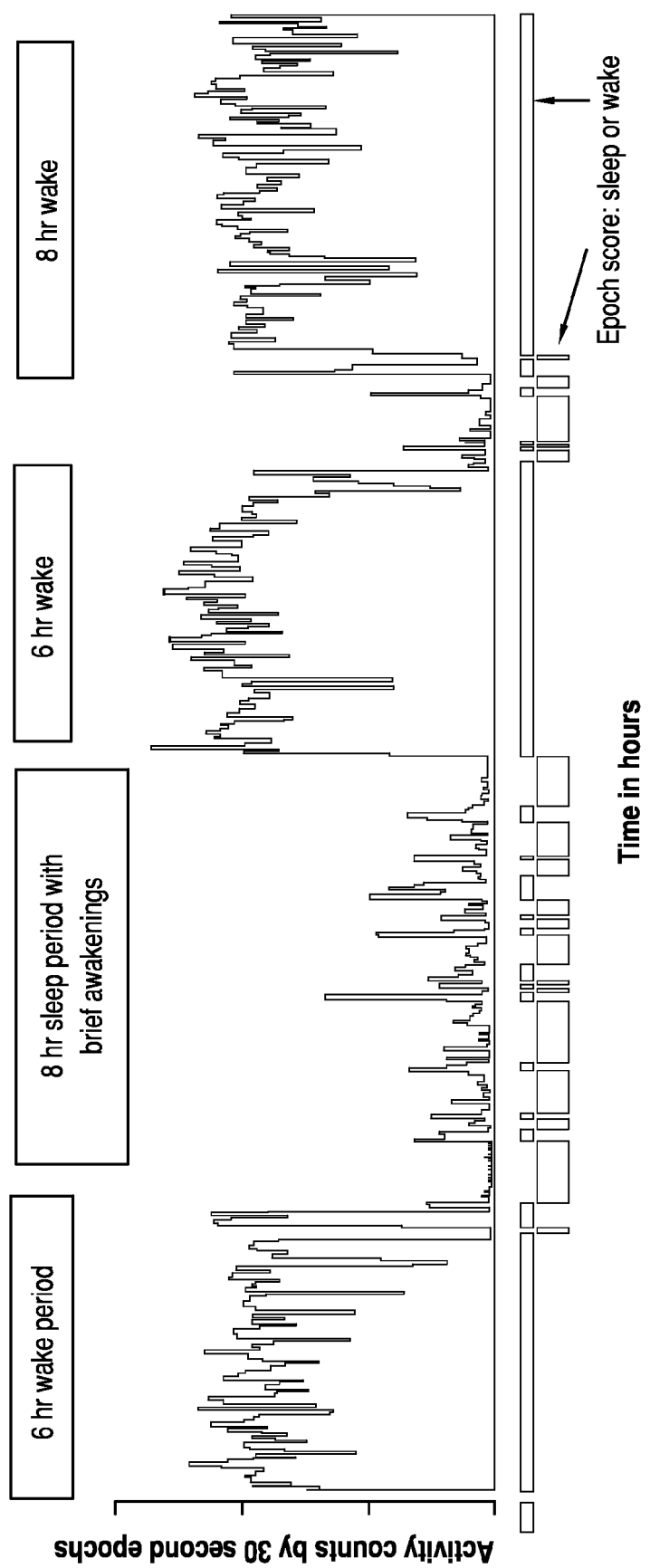

| | | | |
|---|---|---|---|
| 6,582,380 B2* | 6/2003 | Kazlausky et al. | 600/595 |
| 2001/0029319 A1* | 10/2001 | Kazlausky et al. | 600/300 |
| 2002/0017994 A1* | 2/2002 | Balkin et al. | 340/573.1 |
| 2003/0092975 A1 | 5/2003 | Casscells, III et al. | |
| 2006/0217603 A1* | 9/2006 | Nagai et al. | 600/323 |
| 2009/0203972 A1* | 8/2009 | Heneghan et al. | 600/301 |

OTHER PUBLICATIONS

Cole, Roger J., et al., "Technical Note Automatic Sleep/Wake Identification from Wrist Activity", Sleep, 1992, pp. 461-469, vol. 5, No. 5, American Sleep Disorders Association and Sleep Research Society.

Dement, William M.D., et al., "Cyclic Variations in EEG During Sleep and Their Relation to Eye Movements, Body Motility, and Dreaming", Electroencephalogr Clin Neurophysiol, Jun. 3, 1957, pp. 673-690, vol. 9.

Elsmore, T. F., et al., "Monitoring Activity with a Wrist-Worn Actigraph: Effects of Amplifier Passband and Threshold Variations", Naval Health Research Center, Technical Report No. 93-18, pp. 1-63, Jan. 14, 1194.

Redmond, Daniel P., et al., "Observations on the Design and Specification of a Wrist-Worn Human Activity Monitoring System", Behavior Research Methods, Instruments & Computers, 1985, pp. 659-669, vol. 17, No. 6.

Sadeh, Avi, et al., "The Role of Actigraphy in the Evaluation of Sleep Disorders", Sleep, 1995, pp. 288-302, vol. 18, No. 4, American Sleep Disorders Association and Sleep Research Society.

Webster John, B., et al., "An Activity-Based Sleep Monitor System for Ambulatory Use", Sleep, 1982, pp. 389-399, vol. 5, No. 4.

Kelly, Tamsin Lisa, et al., "The Effects of a Single Dose of Pemoline on Performance and Mood During Sleep Deprivation", Military Psychology, 1997, pp. 213-225, vol. 9, No. 3.

* cited by examiner

HUMAN BIOVIBRATIONS METHOD

This patent application is a continuation-in-part application of PCT Application Number PCT/US2007/008219 filed on Apr. 2, 2007 and published in the English language on May 2, 2008. PCT Application Number PCT/US2007/008219 claims the benefit of U.S. provisional patent application No. 60/788,759 filed on Apr. 1, 2006.

I. FIELD OF THE INVENTION

This invention relates to the detection of human biovibrations using a digital signal processing (DSP) actigraph worn by the individual. Human biovibrations result from the human body having reverberations and oscillations from bodily functioning. The DSP actigraph has been shown to be able to identify heart beat and breathing of an individual.

II. BACKGROUND OF THE INVENTION

Actigraphy was originally developed in the 1920s to objectively measure and quantify sleep based on body movements. The first such study was performed in 1922 by Szymansky, who constructed a device that was sensitive to the gross body movements of subjects as they lay in bed. Szymansky J S, *Aktivitaet und ruhe bei den menschen*, Z Angew Psychol 1922; 20:192-222. However, the advent of electroencephalograph (EEG) recording along with the development of EEG-based polysomnographic (PSG) standards for the scoring of sleep stages resulted in a shift away from movement-based measurements of sleep. Dement W, Kleitman N., *Cyclic variations in EEG during sleep and their relation to eye movements, body motility, and dreaming*, Electroencephalogr Clin Neurophysiol 1957; 9:673.

A resurgence of interest in the use of movement-based measurement of sleep occurred when wrist-mounted accelerometry was developed in the 1970s and 1980s at the Walter Reed Army Institute of Research and the National Institutes of Health. Wrist-mounted accelerometers were based on technological advances that, for the first time, made long-term portable measurement and recording of movement data feasible. Redmond D P, Hegge F W, *Observations on the design and specifications of a wrist-worn human activity monitoring system*, Behav Res Methods Instrum Comput 1985; 17:659-69.

The primary research question at the time was whether wrist-mounted actigraphy could reliably and validly measure sleep/wake states in comparison to the EEG gold standard. Several validation studies, using different scoring algorithms, employing subjects with various age ranges, sample sizes, and subjects with sleep and/or movement-related disorders were performed. An early pilot study to address validation issues was conducted by Kripke et al. Kripke D F, Mullaney D J, Messin S, Wyborney V G, *Wrist actigraphic measures of sleep and rhythms*, Electroencephalogr Clin Neurophysiol 1978; 44:674-6. Using five normal subjects, they reported excellent agreement (correlation of 0.98) between actigraphically-derived, manually-scored and polysomnographically-determined measures of sleep duration. Webster et al. published the first algorithm that could be used to automatically score wrist-mounted actigraphic data. Webster J B, Kripke D F, Messin S, et al., *An activity-based sleep monitor system for ambulatory use*, Sleep 1982; 5:189-99. This algorithm was an important development because manually scoring actigraphic data on 30 second epoch-by-epoch bases was labor-intensive and tedious and partially obviated the advantages of the data collection technique. Sadeh, Lavie, et al. applied automatic sleep-wake scoring to home-monitoring of pediatric patients. Sadeh A, Alster J, Urbach D, Lavie P., *Actigraphically based automatic bedtime sleep-wake scoring: Validity and clinical applications*, J Ambul Monit 1989; 2(3): 209-16. They determined a correlation of 85% between conventional polysomography and actigraphically-scored sleep and demonstrated the utility of the wrist-mounted actigraph for ambulatory monitoring. In 1995, Sadeh, Hauri et al. provided a review for the American Sleep Disorders Association (now named the American Academy of Sleep Medicine) that provided validation for the use of wrist-mounted actigraphy as an adjunct in the diagnosis of sleep-related disorders. Sadeh A, Hauri P, Kripke D, Lavie P., *The role of actigraphy in the evaluation of sleep disorders*, Sleep 1995; 18(4):288-302. FIG. 1 shows wrist-mounted actigraphically-determined sleep and wake using a commonly applied algorithm (Action W, Ambulatory Monitoring, Inc, Ardsley, N.Y.). The actigraphy counts are based upon 30 second epochs. The sleep/wake score per epoch is shown below the tracing.

Current conventional actigraph design represents an optimization of past technology based on two key considerations: 1) consistent reliability of the output data (counts of threshold crossings) as input for the detection of sleep/wake state transitions using validated weighted moving average algorithms such as that of Cole et al. Cole R J, Kripke, D F, Gruen W, et al., *Automatic sleep/wake identification from wrist actigraphy*, Sleep 1992; 15(5):461-9; and 2) small size, low weight and power requirements, computational capacity, and other electrical and electronic features realizable as a user-accepted device of reasonable cost. This optimization produces very sharp and deliberate limitations of the information originally contained in the movement signal and passed on to the scoring algorithm. As discussed in Redmond and Hegge (*Observations on the design and specifications of a wrist-worn human activity monitoring system*, Behav Res Methods Instrum Comput 1985; 17:659-69), there are four main areas of design constraint:

1. The sensitivity of the sensor must be such as to respond to "normal" arm movements, but not be "swamped" by the waking movements of a very active person, or by sources of external noise and vibration. This limitation of dynamic range is also a function of digitization, whether it is 8, 12, or 16 bits. Information from very fine, subtle movement is sacrificed.

2. The frequency response of the accelerometric sensor system is sharply confined to a band of 2 to 3 cycles per second (Hz). At the low end, this is to eliminate counts from undulating, slow-wave excursions of the sensor (e.g., due to breathing, or rocking of the device in the gravitational field, or vehicle motion) that are not actually due to motor activity. At frequencies above 3 Hz, this response helps eliminate false counts due to tremor, external noise and vibration, and "ringing" due to sharp impulses.

3. The translation of a complex movement signal into a simple measure, readily computed and expressed digitally in microprocessors of 1985-1995 vintage, resulted in the use of threshold-crossing counts, but eliminated far more descriptive measures of the signal characteristics, such as duration, amplitude, and power.

4. The use of extended (relative to movement rates) periods of measure, i.e., 1- or 2-minute bins, keeps data sets down to workable length in electronic memory, and matches the temporal scale expected by validated sleep/wake algorithms. This integration of sensor data over time smoothes over both rhythmic signals (e.g., tremor) and transient bursts of sensor activity (aperiodic movements). This restriction is advantageous only if such signals are not themselves physiologically relevant.

Recognizing that current usage of wrist-mounted actigraphy thus filtered out a large portion of information contained in the original raw movement signal, the device was redesigned in the early 1990's to permit the automated setting of alternate sensitivities (high [gain=26] and low [5]), counting thresholds (high [24 mV] and low [6 mV]), and frequency response bands (0.1 to 1 Hz, 0.1 to 3 Hz, 0.1 to 9 Hz, 2 to 3 Hz, and 2 to 9 Hz). The design intent was to allow investigation of varied settings (or information content), while normal usage emulated the original, standardized settings. A "trimode" actigraph was thereby developed with activity counts displayed according to three techniques: Zero Crossing Mode (ZCM), Time Above Threshold (TAT), and Proportional Integrative Mode (PIM).

In 1993, Elsmore and Naitoh compared the varied wrist-mounted actigraphy settings against polysomnographically (PSG) scored sleep, using three actigraph/sleep algorithms. Elsmore T F, Naitoh P., *Monitoring of activity with a wrist worn actigraph: effects of amplifier passband and threshold variations*, San Diego, Calif.: Naval Health Research Center; 1993 Feb. Technical Report No.: 93-18. This report confirmed agreement with PSG sleep in the range of 79 to 93% for standard wrist-mounted actigraph settings, using both Cole and Sadeh algorithms. However, the authors found that the broadband frequency settings (0.1 to 3 or 9 Hz) and the low threshold setting produced such high counts in sleep as to render the standard sleep-scoring algorithms useless.

That experience and others reported by Kelly et al., as well as those at Walter Reed Army Institute of Research, point again to a fundamental limitation when using the wrist-mounted actigraph to explore outside the bounds of optimization. Kelly T L, Ryman D H, Schlangen K, et al., *The effects of a single dose of pemoline on performance and mood during sleep deprivation*, Mil Psych 1997; 9:213-25. The chosen settings for gain, threshold, and passband are arbitrary, albeit grounded in the original studies of Redmond and Hegge, with no means of readily adjusting them for comparison's sake while controlling for movement characteristics (system input). Selection of a particular combination of passband, gain, threshold, and digital counting transform automatically selects out other features of the signal's complexity, potentially distorting the original information contained in it, as reported at the output. A systematic approach to this problem requires continuous access to the raw unfiltered signal, and the computational means for parsing, manipulating, and statistically treating its information content.

III. SUMMARY OF THE INVENTION

The application of miniature motion sensors (accelerometers) to study the macro- (gross) and micro- (barely discernible) activities associated with human motion has been termed actigraphy. In countless human sleep studies, actigraphy mostly has been applied to distinguish between when a person is awake or is asleep. Use of wake-sleep information has been applied to the development of mathematical models that aim to predict aspects of cognitive performance. However, wrist-mounted actigraphy potentially has many more applications to cognitive and physical assessment beyond sleep-wake discrimination. For example, studies reveal that micro-miniature accelerometric sensors can discriminate heart rate, breathing, and life cessation (death) via actigraphically-measured biovibration signals. The invention utilizes wrist-mounted actigraphy data showing wrist-monitored ballistocardioimpulses, respirations, and life signs signals. The invention in at least one embodiment uses both the noise and the biovibrations signal as measured from any limb of the body to discern whether an individual is alive or not alive.

The invention includes identification of physiologic microvibrations detected by advanced wrist-mounted actigraph techniques, and how these signals appear to be both a life signs indicator and a potentially quantifiable measure of pain. Respirations and heart rate were identified in the actigraph signal, and removal of cardiac pulsations dramatically reduced the lifesigns signal. Death resulted in cessation of biovibrations.

Human motion contains a wealth of unexplored information. The richness of these biovibrations within the actigraphic signal may be exploited for both continuous physiological monitoring as well as live or dead determination, and may also be used in combination with behavioral and environmental data, as in a vigilance monitor, in order to gain a more detailed understanding of an individual's response to the environment.

The invention includes a method comprising: recording movement data of an individual that includes biovibrations data, determining when the movement data substantially falls within a predetermined threshold representative of death, and providing a notification. In a further embodiment, the invention further includes providing a notification when the oscillations of the movement data decrease over a period of time. In a further embodiment, the invention further includes the threshold having a baseline value.

The invention in at least one embodiment includes a method comprising: monitoring activity counts for zero crossing mode, above threshold mode, and proportional integrative mode, providing a notification when all three activity counts are within a respective predetermined range for a period of time. In a further embodiment, the invention further includes providing medication to an individual being monitored in response to the notification. In a further embodiment, the invention further includes setting the predetermined time to at least 15 minutes. In a further embodiment, the invention further includes setting the predetermined range to a maximum of 90% of the average activity count of the preceding hour. In a further embodiment, the invention further includes setting the predetermined range to a minimum greater than 10% of the average activity count of the preceding hour. In a further embodiment, the invention further includes setting the predetermined range above activity counts representative of sleep.

The invention in at least one embodiment includes a method comprising: monitoring activity counts for zero crossing mode, above threshold mode, and proportional integrative mode of a patient, determining the activity count level for the patient when asleep, and providing medication when at least two of the duration, frequency and level of at least two of the activity counts during a current sampling period is lower than the prior sampling period but above the activity counts associated with sleep for the patient being monitored.

Given the following enabling description of the drawings, the apparatus should become evident to a person of ordinary skill in the art.

IV. BRIEF DESCRIPTION OF THE DRAWINGS

FIG. 1 illustrates conventional wrist-mounted actigraph tracing with sleep scoring algorithm applied over a 28 hour period. Activity within each 30-second epoch is counted. An epoch is scored as wake if an activity is above a preset threshold and as sleep if activity is below that threshold. Using current algorithms, an individual sleeping in a moving vehicle could be considered awake, and an individual in a coma could be considered asleep.

Figure 2:
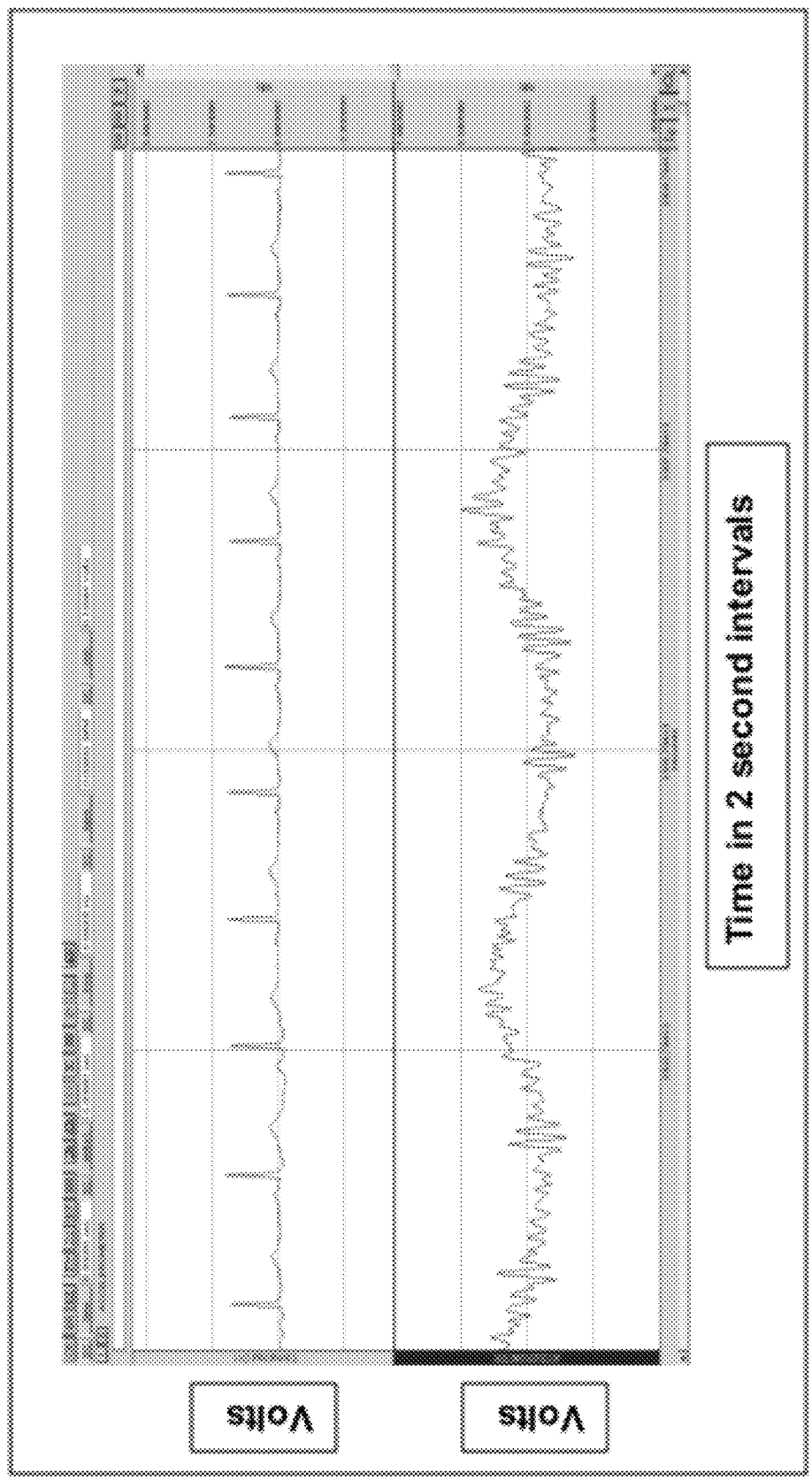

FIG. 2 illustrates electrocardiogram (ECG; upper panel) and wrist-mounted, advanced digital signal processing (DSP) actigram (lower panel) in a Walter Reed Army Medical Center patient under deep anesthesia, time synchronized over an 8-second period with time shown in 2 second intervals. DSP actigram shows ballistocardiobursts called W-waves following ECG-recorded heart rate by several milliseconds, microtremor as high-frequency low amplitude background activity, and respirations as low-amplitude low-frequency sinusoidal waves.

Figure 3:
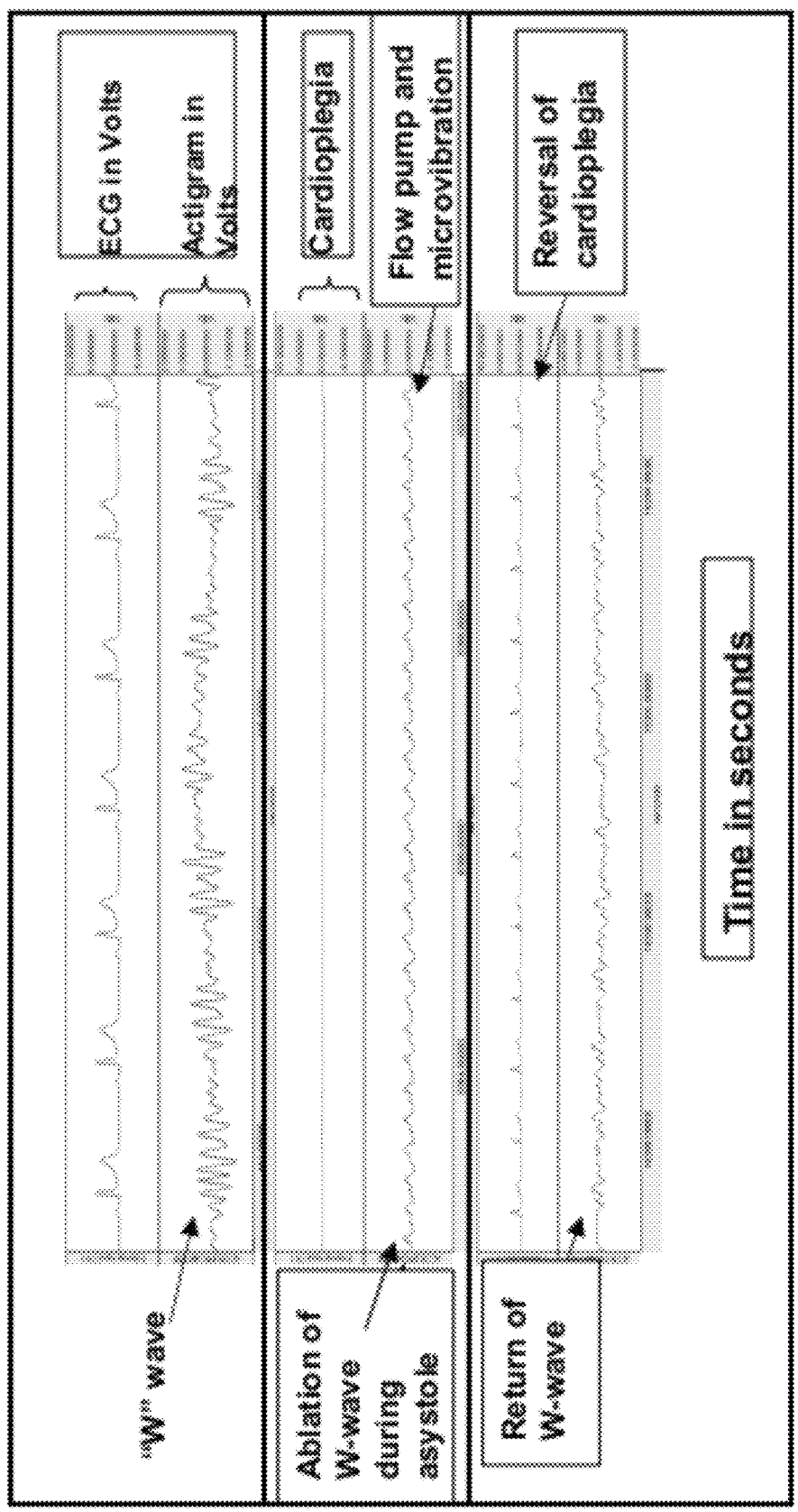

FIG. 3 illustrates elctrocadiogram (ECG; upper tracings in each panel) and wrist-mounted, advanced DSP actigram (lower tracings) in a Walter Reed Army Medical Center patient undergoing cardiopulmonary bypass surgery with time shown in seconds. The upper panel shows ECG wave preceding each cardioballistic W-wave. The middle panel shows period when the patient is on a cardiac flow pump, with ablation of both ECG and actigram ballistocardiobursts. The rhythmic mechanical signature of the flow pump and low-amplitude physiological microvibration remain apparent. The lower panel shows return of ECG and actigraphic ballistocardiobursts following disconnection of bypass pump and return of systole.

Figure 4:
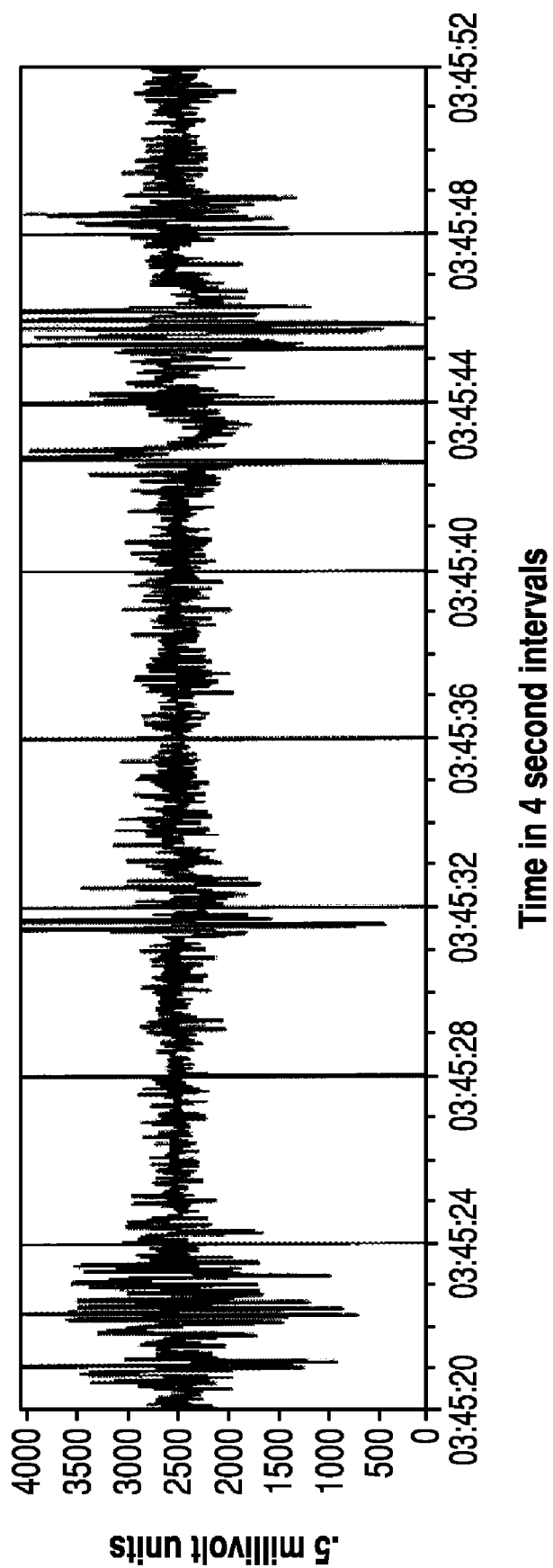

FIG. 4 illustrates an actigram from a patient at Walter Reed Army Medical Center in a Glasgow level 8 coma, as measured by wrist-mounted, advanced DSP actigraph over a 30 second period with time intervals showing 4 second intervals. Large bursts are spontaneous limb movements. Small regular-interval bursts are cardioballistic pulsations. High-frequency low-amplitude background activity is life-signs biovibration.

Figure 5:
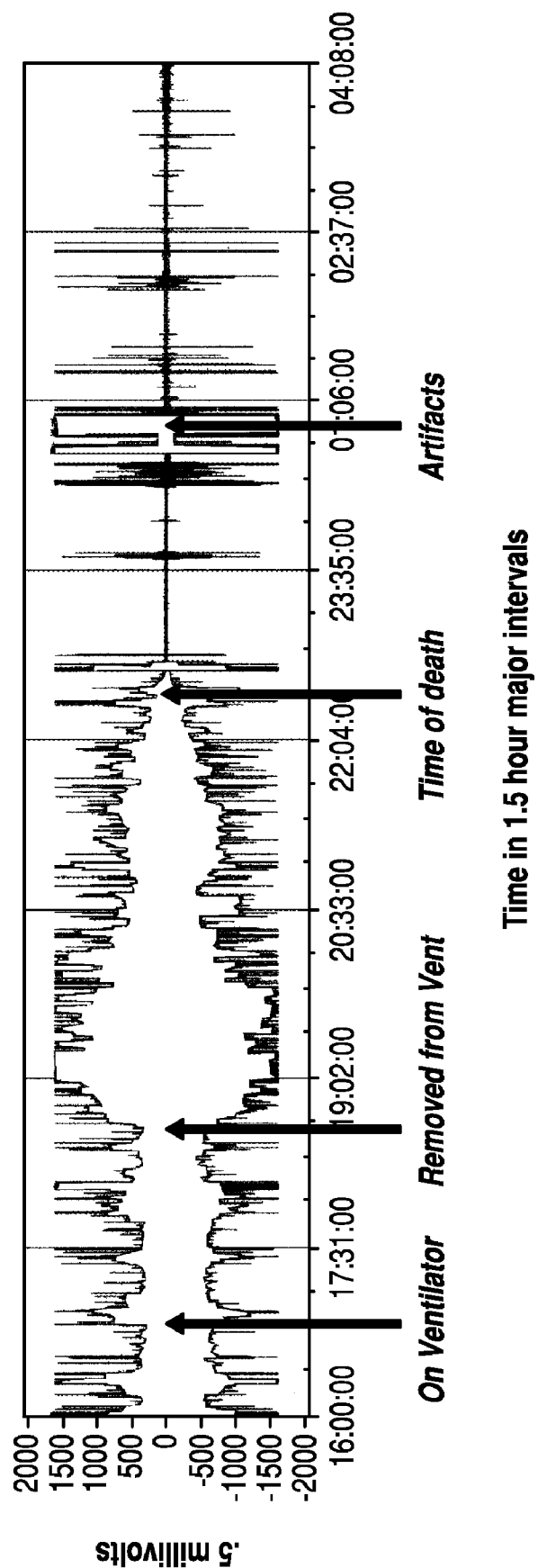

FIG. 5 illustrates an actigram from wrist-mounted, advanced DSP actigraph over a 12-hour period in a patient transitioning from deep coma to death with time intervals at 1.5 hours. Note the high-density signal prior to death, and flat line (no signal) following death. Note that following removal from ventilator, core activity increases then gradually tapers to the point of cessation.

Figure 6:
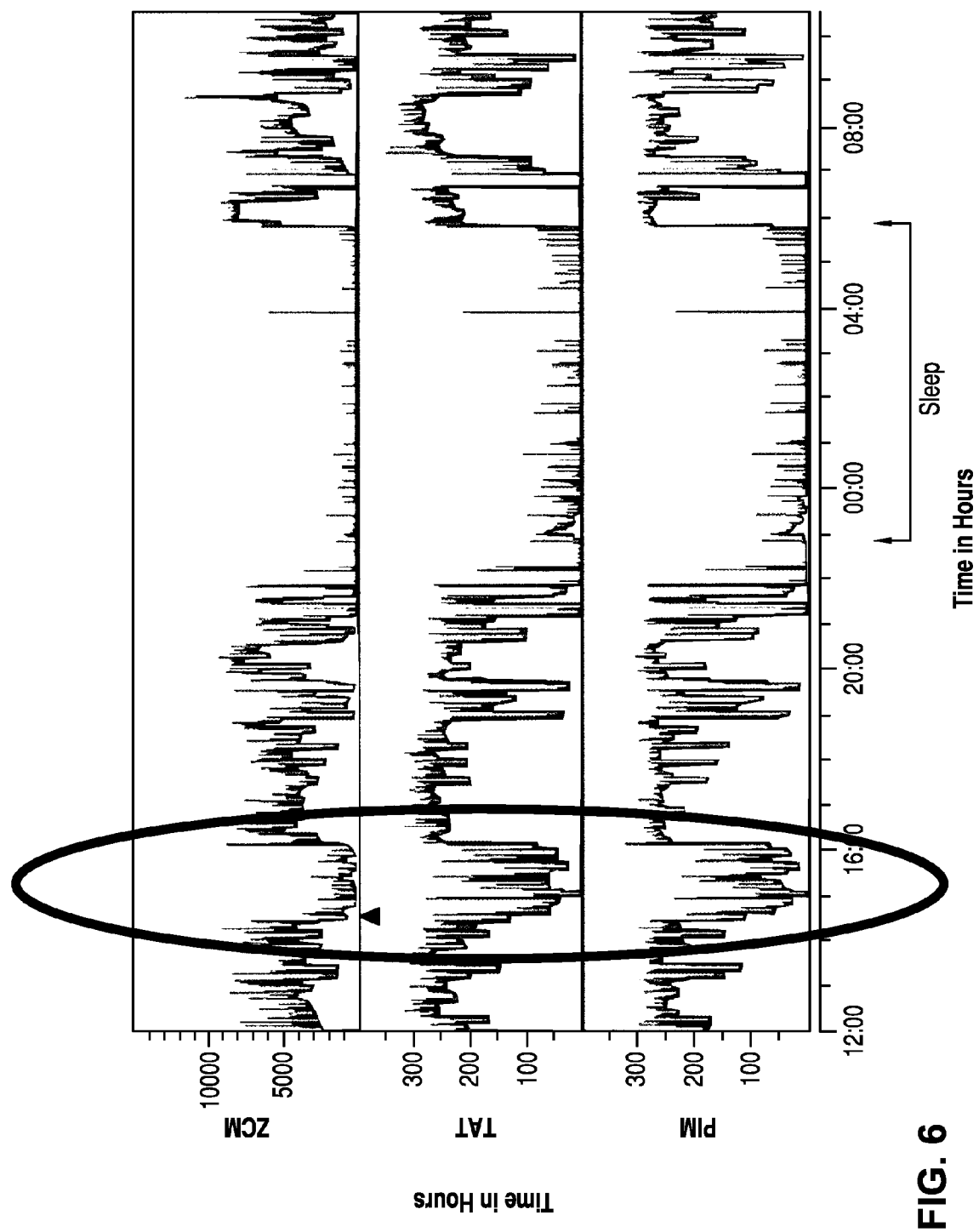

FIG. 6 illustrates an actigraph tracing of a migraine episode recorded across three channels using a wrist-mounted tri-mode actigraph. Note the period of hypo-kinetic activity as distinguished from wake and sleep patterns. Migraine onset marked with an arrow. The top panel shows zero crossing mode (ZCM), the middle panel shows time above threshold mode (TAT), and the bottom panel shows proportional integrative mode (PIM).

Figure 7:
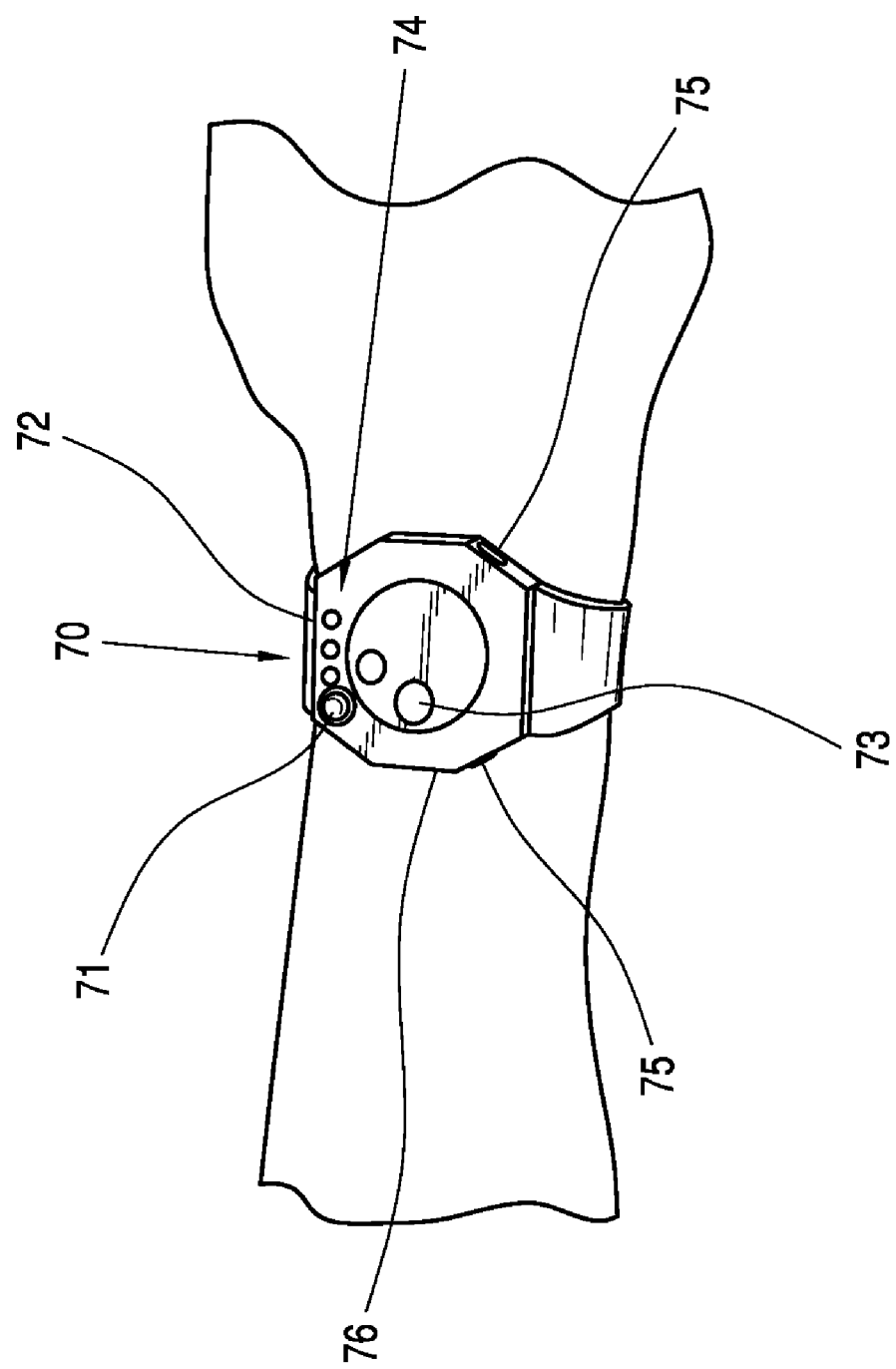

FIG. 7 illustrates a wrist-mounted vigilance, activity, and environmental monitor. The sensors, stimulus presentation capability, and response buttons are identified. The illustrated device includes the capability to provide vibratory stimuli similar to pagers or cell phones.

Figure 8:
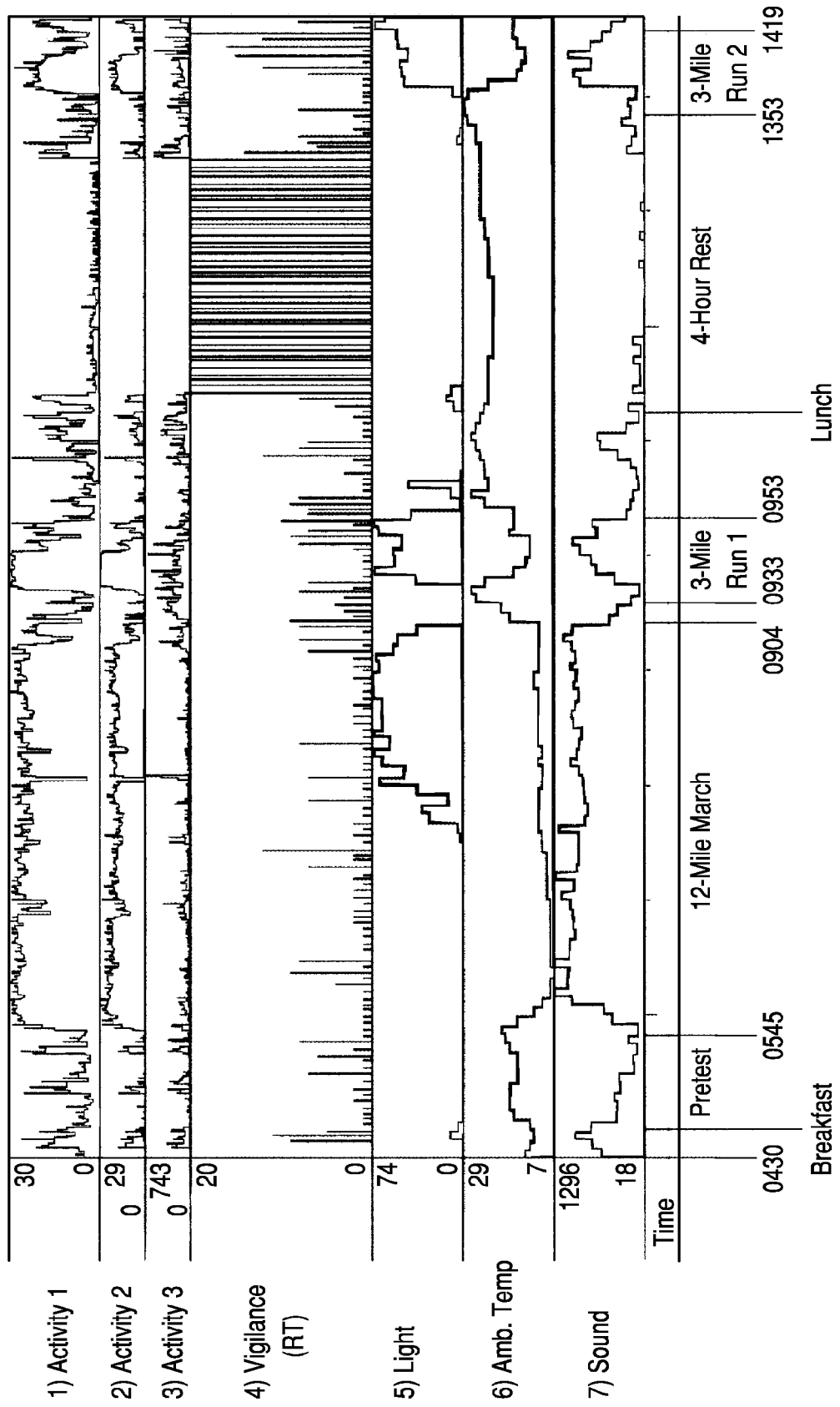

FIG. 8 illustrates representative wrist-mounted vigilance and activity monitor data from one subject continuously collected over 10 hours of a field exercise. The seven channels of data that were acquired are labeled individually on the x-axis. Activities in which the volunteer was participating and clock hours are indicated on the lowest y-axis. Channels 1-3: these three channels, labeled "Activity 1-3," respectively, are sensing physical motion (acceleration). The data are similar to a standard actigraph-tracing. The vertical height of each line plotted on the x-axis represents the number of movements detected in 1 minute of time. Each channel is optimized to detect motion with different physical characteristics. The first and second channels of activity data vary with regard to the amplitude of the acceleration to which they are sensitive. The third channel was sensitive to longer duration accelerations. Channel 4: the fourth channel, labeled "Vigilance (RT)," displays the response of the subject in second to the presentation of a sequence of tones at random intervals. The height of each bar represents the speed of response to the tone. When a bar reaches to the top of its graph, this indicates that subject did not respond to that stimulus. Channel 5: this channel, labeled "Light," is the illumination level recorded at the wrist of the subject in arbitrary units. Channel 6: the temperature channel, labeled "Amb. Temp.," continuous records ambient temperature in degrees Celsius on the subject's wrist. Channel 7: this channel, "Sound," continuously records ambient sound levels in arbitrary units (24).

V. DETAILED DESCRIPTION OF THE DRAWINGS

The invention provides an enhanced ability for health care providers to remotely monitor the health status or identify an individual soldier on the battlefield or a person operating under extreme environmental conditions. The invention provides an individualized capability to provide neuron-physiologic input for medical decision-making. Human biovibrations can potentially be used to provide objective measures necessary for the healthcare provider to assess the efficacy of medications aimed at controlling pain. The invention by using a digital signal processing (DSP) actigraph can measure fine motor micro-movements to the degree necessary to assess human biovibrations and apply them as indicator of individuality to determine, for example, a live/dead detection capability or to assist, for example, with pain management techniques by providing objective measures (i.e., muscular contractions) to facilitate pain management interventions.

A general-purpose ballistic wrist-mounted actigraph, one that will work across a broad range of signal waveforms, has recently been used to detect and quantify physiological microvibration characteristics. This wrist-mounted Advanced Digital Signal Processing (DSP) actigraph (Precision Control Design, Inc. Fort Walton Beach, Florida) allows recording and characterization of individual movements and patterns of movements without destroying the information contained within them. Such features as duration, waveshape, amplitude, and component frequencies may be used to describe movements as they occur. These features may be saved and analyzed in relation to sleep, fatigue, exposure to neuro-motor toxins, or specific environmental conditions. Currently no real-time monitoring capability exists for these applications.

This state-of-the-art digital signal processing wrist-mounted actigraphy technology attempts to utilize detailed accelerometric information which had previously been discarded. For example, current studies are demonstrating very low-level respiratory and ballistographic signatures. Low frequency breathing movements from analysis of the signal within a 0.1 to 3 Hz bandwidth are seen (FIG. 2) although breathing can be determined using a 0.1 to 1 Hz bandwidth. Ballistocardiobursts follow electrocardiographic signals by several milliseconds in synchronized tracings (FIGS. 2 and 3). The time-linked relationship indicates consistency between the chest-recorded cardiac-generated electrical signals and the wrist-recorded flow-generated pulse waves. The flow-generated pulse waves often appear in shape of a "W" possibly reflecting soft tissue oscillation. Ablation of both cardioballistic and respiratory signals is apparent when the heart and ventilation are stopped (FIG. 3, middle panel) during coronary bypass surgery. The return of the W-wave may be seen when cardiopulmonary bypass is terminated and the heart begins beating again. (FIG. 3, final panel).

Motion signals are captured along a range of frequencies, referred to as the bandpass. When the bandpass filters are configured to record motion in the 0.1 to 9 Hz frequency range (alternatively the frequency range is 0.1 to 14 Hz), and sensitivity is maximized, the wrist-mounted actigraph registers non-zero counts continuously, so long as the device is being worn. This activity may be considered a lifesigns signal, and may be related to the microvibrations described by Rohracher. According to Rohracher, a low-level tremor occurs in the frequency band of 7.5 to 12.5 Hz, and is readily detected by wrist-mounted actigraphy. Bircher et al. considered that alterations in these microtremors may be related to body stress levels. Our hypothesis is that these microvibrations may be the peripherally measured motion associated with rhythmic physiologic activities. As such, they may be responsive to stress level and circadian changes. For example, components of the signal may reflect the peripheral effects of changing cortisol levels. As may be seen in FIG. 3, the largest component of this lifesigns signal is the heartbeat, with lesser contributions from gastrointestinal, respiration, and skeletal muscle activities. As such, this signal can be used as an essential indicator of life.

Neurophysiological signals have historically been measured in the clinical setting by application specific technologies. Electromyography (EMG) for example provides objective monitoring of single muscle characteristics, while electroencephalography (EEG) through the array of scalp applied electrodes can often localize the brain region responsible for seizure activities. EMG and EEG provide perhaps the most accurate and regionally focused measures of motor and cortical activities, but are technically complex and with regard to EMG, sometimes invasive. They require trained physicians and technicians, expensive equipment, and are often difficult to utilize in ambulatory settings. The application of digital signal processing wrist-mounted actigraphy may enable ambulatory monitoring of the peripheral manifestations of aspects of neurophysiological signals. In no way, however, would actigraphy be able to identify characteristics of electrocortical or muscle fiber signals in themselves, rendering wrist-mounted actigraphy a complementary technology, not an alternative technology.

Wrist-mounted actigraphy has not proven to be a panacea for clinical medicine. The difficulty in distinguishing physiological signals from artifact has proved challenging with regard to the applications of wrist-mounted actigraphy in clinical settings. For example, attempts to apply wrist-mounted actigraphy in Parkinson's disease (PD) patients identified difficulties in distinguishing among tremor, slow movements (bradykinesia), rigidity, and normal ambulatory activity. Tremor may be studied most easily in a PD model, where the characteristics of the tremor have been widely described, and the pathophysiology of the disease well understood. Van Someren et al. designed and tested techniques to specifically detect and quantify parkinsonian tremor, with some success. Due to technical limitations of earlier actigraphs, their versatility in response to varied settings and fluctuations in tremor characteristics were restricted. Non-actigraphic methods of objectively evaluating the severity of PD symptoms such as EMG, remain technologically demanding, logistically difficult, and impractical for long-term daily/routine use, therefore advanced digital signal processing wrist-mounted actigraphy should be considered as a potential alternative.

Some medical conditions have clear relevance in military and operational environments. Seizure is an example of an operationally relevant condition that could potentially be characterized by wrist-mounted actigraphy. Seizures may occur as a result of chemical agent exposures or head trauma, as a potential consequence of excessive stimulant use (such as with amphetamines), or as a manifestation of fear and stress (pseudo-seizures). Seizures are currently diagnosed by EEG. If biovibration patterns were identified for specific seizure types, digital signal processing wrist-mounted actigraphy would offer the potential for ambulatory screening of some seizure types at a reduced cost. Actigraphy can not replace EEG as a technique to assess electrocortical activities for localization of seizure origin.

Coma also is an example of a militarily relevant condition, with causes as diverse as hypoxia, trauma, infectious or nerve agent exposure. Coma is under study by digital signal processing wrist-mounted actigraphy for the purpose of distinguishing, through biovibration characteristics, its different levels and its differences from sleep. FIG. 4 shows an actigram of a patient in Glasgow Coma level 8 from a study at Walter Reed Army Medical Center. Large amplitude bursts are spontaneous limb movements. Small low amplitude regular-interval bursts are cardioballistic pulsations. High frequency very low amplitude background activity is life signs biovibration, hypothesized to be the summation of internal systemic reverberation.

Other data from this study demonstrate that life and death may be differentiated. FIG. 5 shows an actigram of a patient in Glasgow Coma level 3 transitioning from life to death. The first third of the 12 hour tracing shows the ventilator-assisted patient manifesting an inherent biovibration of approximately 0.5 volt amplitude, interrupted by regularly-spaced higher amplitude artifacts representing nursing staff interventions. At approximately 2.5 hours into the tracing, ventilator support is removed. The intrinsic biovibration signal plumes over 20 minutes to an amplitude of approximately 1.5 volts, where it remains for almost 20 minutes before beginning a 60 minute taper to the baseline amplitude of approximately 0.5 volts. Over the next 40 minutes the signal remains relatively stable before beginning an 80 minute taper to a point of cessation.

Pain is another example of a condition for which there is operational and military interest in objective diagnosis and treatment. Current methods of grading and treating pain rely upon subjective quantification by the patient. Preliminary data using trimode wrist-mounted actigraphy from Walter Reed Army Medical Center reveal that migraine headache pain has a distinct oscillation pattern (FIG. 6). The patient reported during the migraine a slowing of all activities, with a decreased duration, frequency, and magnitude of coarse body movements. The patient was clearly awake, but activity pattern altered perceptibly during the headache period. Interestingly, during the nights following migraine, despite resolution of the headache, sleep was fragmented and there was loss of the usual circadian activity rhythm. This is the first time that pain has been shown to have a distinct signal capable of quantification.

Digital signal processing wrist-mounted actigraphy can quantify the components of macro- and micro-activities unique to specific types of pain, which means treatment effectiveness can potentially be assessed through changes in biovibration patterns. For example, biovibration monitoring may be able to provide feedback for automated pain therapy infusion pumps for burn- or cancer-induced pain.

Wrist-mounted actigraphs are not yet ready for arduous operational applications. The battlefield and space environments are rich in vibration and movement, and any projected use of a sensitive motion monitor would require algorithms to discern mechanical vibration patterns from physiological patterns. Techniques have not yet been developed to reliably cancel mechanical motion in real time. The rolling and bouncing movement of ground vehicles, and the high vibration of rotary wing aircraft, and the pitching and reverberation movements of fixed wing aircraft all produce mechanical noise that would interfere with a sensitive motion sensor's ability to discern physiological macro- or micro-vibrations.

Rudimentary algorithms exist to cancel specific components of the mechanical vibration, but thus far there is no systematic study of this problem and no algorithm to completely mitigate the mechanical noise effects in real time. Field tests of a performance prediction model in fixed-wing military crews showed that conventional wrist-mounted actigraph data was overwhelmed by mechanical noise during flight operations. Consequently, sleep scoring algorithms for performance prediction are not currently reliable in moving ground, sea-based, or aerial vehicles.

High fidelity vibration-cancellation techniques applied towards actigraphically-acquired data would improve sleep-wake state determination in mobile platforms, but might not in themselves provide the ability to predict cognitive performance in high vibration environments. High intensity vibration, as is found in rotary wing platforms, can in itself elicit cognitive impairment in some individuals. Mechanisms of identifying these individuals and algorithms to consider the effects of mechanical vibration on cognition may find a place in prediction models that assess cognitive performance. In 1976 Graybiel and Knepton coined the phrase "Sopite Syndrome" to define a subset of people who become tired or lethargic from motion but do not suffer from symptoms such as nausea or vomiting. Graybiel and Knepton noticed a variety of other related symptoms: apathy, decreased ability to concentrate, daydreaming, melancholy, sleep disturbances, performance errors, frequent daytime napping, and irritability. Little is known about the potential impact of the Sopite Syndrome on cognitive performance in civil and military aviation. Some evidence shows that airline cabin crews suffer from post-flight fatigue and sleeping problems more often than cockpit crews despite being less confined. Strongin and Charlton hypothesized that with exposure to fewer external visual references concerning the true direction of the plane and reduced continuous sensory feedback typically associated with pilots' commands on the craft, the cabin aircrews were more susceptible to Sopite Syndrome. Motion sickness symptoms that occur in passengers during enclosed-cabin ground vehicle transport may have similar origins to those hypothesized by Strongin and Carlton for aviation passengers.

Cognitive performance degradation in operational environments has a multitude of causes beyond mechanical vibration, sleep deprivation and circadian factors, to include rate of energy utilization versus caloric replenishment, ambient and core body temperatures, altitude associated relative oxygenation, and intensity of ambient light. Integrating the contributions of these and other factors with wrist-mounted actigraphic measures of sleep and wake may provide more comprehensive data for models that predict cognitive performance.

A device that could measure activity in the field, assess environmental conditions, and simultaneously monitor cognitive performance would have considerable utility, especially in field studies, and has been developed at the U.S. Army Research Institute of Environmental Medicine (US-ARIEM). Since USARIEM's mission is to investigate the effects of the environment on soldier performance, their investigators have integrated wrist-mounted actigraphy with assessment of vigilance, reaction time, ambient temperature, humidity, light and sound.

One of the first studies employing the wrist-mounted vigilance-monitor-actigraph assessed the effects of a nutritional intervention on soldiers engaged in a training exercise designed to simulate a brief, but intense, light infantry mission. In that study the devices successfully documented the beneficial effects of a carbohydrate beverage on vigilance. A device capable of facilitating the invention is pictured in FIG. 7 and data collected from a representative volunteer during that simulated infantry mission are presented in FIG. 8.

FIG. 7 illustrates a wrist-mounted vigilance, activity, and environmental monitor 70. The illustrated monitor 70 includes a variety of sensors for detecting different environmental conditions and interfaces for interacting with the wearer. The sensors include an ambient illumination sensor 71 to detect the level of light, an ambient sound sensor 72, and an ambient humidity and temperature sensor 73. The interfaces include a set of three LEDs 74 to provide visual stimuli, a pair of side response buttons 75, a speaker 76 to provide auditory stimuli, and internal to the device a vibratory mechanism.

The most unique capability of the wrist-mounted vigilance-monitor-actigraph is its capability to assess vigilance and reaction time as illustrated by Channel 4 of FIG. 8. Vigilance is assessed by randomly presenting a series of auditory stimuli and recording, by button-press, a response (or lack thereof) to these tones. Since the device 70 illustrated in FIG. 7 is fully programmable, it could potentially assess a wide variety of cognitive functions including learning, memory, pattern recognition, and reasoning, if the investigator wished to do so. In addition, as the device can measure multiple types of movement activity, as shown in FIG. 8, Channels 1-3, as defined by their frequency components, it may be useful for assessing energy expenditure, an important objective in nutritional research.

Exposure to extreme cold weather is a condition of concern in some operational environments, as it and/or water immersion can lower body temperatures and adversely impact performance by increasing the risk of cold injury and reducing physical and cognitive abilities. Prediction of core body temperatures during exercise in cold water using thermoregulatory models is based on limited data. Many different factors have a role in body core temperature responses during cold-water immersion. These include a) water temperature, b) immersion depth, c) body fat, and d) metabolic rate. A decrease in water temperature increases the thermal gradient between the person and the environment and leads to significantly greater heat loss via convection and conduction. The greater the depth a person is immersed in water, the greater the effective body surface area for heat exchange between the person and the water, which will cause core temperature to decrease more rapidly. People with higher body fat percentages tend to lose heat less rapidly than thin people in cold water.

Heat production in response to hypothermia is assumed to come from an initiation of involuntary motor activity—shivering, as an attempt to prevent the reduction of core body temperature. Detection of shivering has to date consisted of either visual inspection or the use of electromyography. Assessment of shiver; however, has been tenuous at best and has been heavily dependent on observations and grading of shivering on various rating scales. These scales vary in criteria, contain limited discrete values, and are often subjected to rater bias. The more objective techniques such as EMG have been used to quantify shivering and in fact fuel utilization because shivering can be discerned by the EMG burst activity due to shivering. However, these measurements are hampered by their intrusiveness. Whether the shivering activity is predictive of a person's thermoregulatory status/body temperature is unknown, but is currently an area under investigation through specifically designed actigraphs. Off-the-shelf wrist-mounted actigraphs are usually not designed for water immersion. Biovibration characteristics as captured through water-proofed wrist-mounted DSP actigraphy may enable investigators to quantify these shivering responses.

The invention can take the form of an entirely hardware embodiment, an entirely software embodiment or an embodiment containing both hardware and software elements. In at least one exemplary embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium such as carrier signal. Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Computer program code for carrying out operations of the present invention may be written in a variety of computer programming languages. The program code may be executed entirely on at least one computing device, as a stand-alone software package, or it may be executed partly on one computing device and partly on a remote computer. In the latter scenario, the remote computer may be connected directly to the one computing device via a LAN or a WAN (for example, Intranet), or the connection may be made indirectly through an external computer (for example, through the Internet, a secure network, a sneaker net, or some combination of these).

It will be understood that each block of the flowchart illustrations and block diagrams and combinations of those blocks can be implemented by computer program instructions and/or means. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowcharts or block diagrams.

The exemplary and alternative embodiments described above may be combined in a variety of ways with each other. Furthermore, the steps and number of the various steps illustrated in the figures may be adjusted from that shown.

It should be noted that the present invention may, however, be embodied in many different forms and should not be construed as limited to the embodiments set forth herein; rather, the embodiments set forth herein are provided so that the disclosure will be thorough and complete, and will fully convey the scope of the invention to those skilled in the art. The accompanying drawings illustrate exemplary embodiments of the invention.

Although the present invention has been described in terms of particular exemplary and alternative embodiments, it is not limited to those embodiments. Alternative embodiments, examples, and modifications which would still be encompassed by the invention may be made by those skilled in the art, particularly in light of the foregoing teachings.

As used above "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

Those skilled in the art will appreciate that various adaptations and modifications of the exemplary and alternative embodiments described above can be configured without departing from the scope and spirit of the invention. Therefore, it is to be understood that, within the scope of the appended claims, the invention may be practiced other than as specifically described herein.

We claim:

1. A method comprising:
   monitoring activity counts for zero crossing mode, above threshold mode, and proportional integrative mode of an individual with an actigraph,
   providing a notification when the activity counts for zero crossing mode, above threshold mode, and proportional integrative mode are within a respective predetermined range for a period of time.

2. The method according to claim 1, further comprising:
   providing medication to an individual being monitored in response to the notification.

3. The method according to claim 1, wherein the period of time is at least 15 minutes.

4. The method according to claim 1, wherein the predetermined range has a maximum of 90% of an average activity count over a preceding hour.

5. The method according to claim 4, wherein the predetermined range has a minimum greater than 10% of the average activity count of the preceding hour.

6. The method according to claim 1, wherein the predetermined range is above activity counts representative of sleep.

7. The method according to claim 6, wherein when the predetermined range is reached, a patient being monitored is suffering pain.

8. The method according claim 6, wherein when a duration and frequency of the activity counts are decreased in a period of time as compared to a preceding period of time, the notification includes an indication of a migraine.

9. The method according to claim 1, further comprising providing a migraine notification when a duration and frequency of the activity counts are decreased in a period of time as compared to a preceding period of time.

10. The method according to claim 1, wherein the predetermined range has a minimum greater than 10% of an average activity count over a preceding hour.

11. The method according to claim 1, further comprising analyzing an effectiveness of medication for relieving a migraine based on a reduction of fragmentation in sleep in at least one night following the migraine.

12. The method according to claim 1, further comprising:
   determining presumptive death when zero crossing mode is null for at least two minutes, and
   determining definitive death when zero crossing mode is null for at least five minutes.

13. The method according to claim 1, wherein the actigraph provides the notification.

14. A method comprising:
   monitoring activity counts for zero crossing mode, above threshold mode, and proportional integrative mode of a patient with an actigraph,
   determining the activity count levels for the patient when the patient is asleep, and
   providing medication when at least two of a duration, a frequency and a level of at least two of the activity counts during a current sampling period are lower than the prior sampling period but above the activity counts associated with sleep for the patient being monitored.

15. The method according to claim 14, wherein the actigraph determines the activity count.

16. The method according to claim 14, wherein a processor determines the activity count.

17. A method comprising:
   recording movement data of an individual that includes biovibrations data with an actigraph,
   determining when the movement data substantially falls within a predetermined threshold representative of death, and
   providing a notification.

18. The method according to claim 17, further comprising:
   providing a notification when oscillations of the movement data decrease over a period of time.

19. The method according to claim 17, wherein the predetermined threshold is a baseline value.

20. The method according to claim 17, wherein the actigraph determines when the movement data substantially falls and provides a notification.

* * * * *